(12) United States Patent
Ishida et al.

(10) Patent No.: US 8,299,288 B2
(45) Date of Patent: Oct. 30, 2012

(54) METHOD FOR PRODUCING α-HYDROXYESTER COMPOUND

(75) Inventors: Hajime Ishida, Saijo (JP); Masaji Hirota, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/060,169

(22) PCT Filed: Aug. 24, 2009

(86) PCT No.: PCT/JP2009/065130
§ 371 (c)(1),
(2), (4) Date: Feb. 22, 2011

(87) PCT Pub. No.: WO2010/024419
PCT Pub. Date: Mar. 4, 2010

(65) Prior Publication Data
US 2011/0144372 A1    Jun. 16, 2011

(30) Foreign Application Priority Data
Aug. 26, 2008  (JP) ................................. 2008-216358
Jan. 23, 2009  (JP) ................................. 2009-012863

(51) Int. Cl.
*C07C 67/22*  (2006.01)
*C07C 69/732*  (2006.01)
*C07C 257/06*  (2006.01)

(52) U.S. Cl. ............................................. 558/6; 560/60
(58) Field of Classification Search ................. None
See application file for complete search history.

(56) References Cited

U.S. PATENT DOCUMENTS

| | | | | |
|---|---|---|---|---|
| 2,892,847 A * | 6/1959 | Wagner | ........................ | 549/469 |
| 5,145,480 A * | 9/1992 | Wang | ............................... | 482/63 |
| 5,145,980 A * | 9/1992 | Wenderoth et al. | ............. | 560/35 |
| 5,221,762 A * | 6/1993 | Wingert et al. | ................ | 560/35 |
| 5,948,819 A * | 9/1999 | Ohtsuka et al. | ............... | 514/617 |
| 2003/0153728 A1* | 8/2003 | Kolb et al. | .................... | 530/331 |
| 2006/0160828 A1 | 7/2006 | Malamas et al. | | |
| 2011/0034718 A1* | 2/2011 | Nakazawa | ..................... | 558/351 |

FOREIGN PATENT DOCUMENTS
JP       2008-526966 A      7/2008

OTHER PUBLICATIONS

Fosdick et al. "Some Alkyl and Alkamine Esters of p-Amnomandelec Acid and Related Compounds", Journal of the American Chemical Society, 60, 1465-1466, 1938.*
Baeza et al "Enantioselective Synthesis of O-Methoxycarbonyl Cyanohydrins: Chiral Building Blocks Generated by Bifunctional Catalysis with BIONOLAM-AlCl", European Journal of Organic Chemistry, 1949-1958, 2006.*
Fosdick et al., "Some Alkyl and Alkamine Esters of p-Aminomandelic Acid and Related Compounds", Journal of the American Chemical Society, 60, 1465-1466, 1938.*
Journal of the Chemical Society, Perkin Transactions 1: Organic and Bio-Organic Chemistry, 1999, 19, 2677-2689.*
Christian R. Noe, "Chiral Lactols, II: Racemate Separation and Enantioselective Acetalization with the 2, 3, 3a, 4, 5, 7, 7a-octahydro-7, 8, 8-trimethyl-4, 7-methanobenzofuran-2-yl Protective Group", Chemische Berichte, 1982, pp. 1591-1606, vol. 115, No. 4.

* cited by examiner

*Primary Examiner* — Fiona T Powers
(74) *Attorney, Agent, or Firm* — Sughrue Mion, PLLC

(57) ABSTRACT

Disclosed is a method for producing a compound represented by Formula (4), the method including Step I of adding a solution in which hydrogen chloride is dissolved in an alcohol, to a mixture containing an organic solvent and a compound represented by Formula (1), and Step II of mixing a compound obtained in Step I, represented by Formula (3), with water.

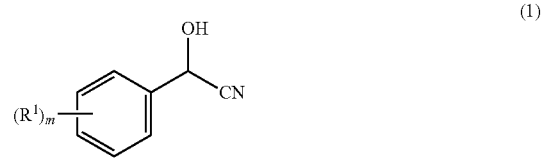

(1)

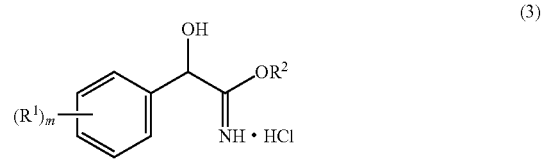

(3)

8 Claims, No Drawings

METHOD FOR PRODUCING α-HYDROXYESTER COMPOUND

CROSS REFERENCE TO RELATED APPLICATIONS

This application is a National Stage of International Application No. PCT/JP2009/065130 filed Aug. 24, 2009, which claims priority from Japanese Patent Application No. 2008-216358 filed Aug. 26, 2008 and Japanese Patent Application No. 2009-012863 filed Jan. 23, 2009, the contents of all of which are incorporated herein by reference in their entirety.

TECHNICAL FIELD

The present invention relates to a method for producing an α-hydroxyester compound.

BACKGROUND ART

As a method for producing an α-hydroxyester compound from a cyanohydrin compound, for example, JP-A-4-230241 discloses a method in which a hydrogen chloride gas was fed to a solution in which a cyanohydrin compound is dissolved in an alcohol, and then water is added. PCT International Publication No. WO 2007/018221 Pamphlet discloses a method in which a hydrogen chloride gas is fed to a mixture containing a cyanohydrin compound, an alcohol and water.

DISCLOSURE OF THE INVENTION

An object of the present invention is to provide a method capable of producing an α-hydroxyester compound in a satisfactory yield.

The present inventors have intensively studied and found that the above object can be achieved by adding a solution in which hydrogen chloride is dissolved in an alcohol having 1 to 4 carbon atoms, to a mixture containing an organic solvent and a predetermined cyanohydrin compound, thus leading to the present invention.

The present invention relates to the invention as follows.

[1] A method for producing a compound represented by Formula (4):

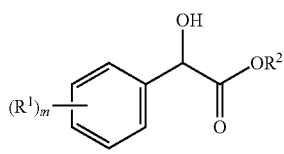
(4)

wherein $R^1$, $R^2$ and m each represent the same meanings as defined below, which comprises Step I of adding a solution in which hydrogen chloride is dissolved in an alcohol represented by Formula (2):

$R^2OH$ (2)

wherein $R^2$ represents an alkyl group having 1 to 4 carbon atoms, to a mixture containing organic solvent and a compound represented by Formula (1):

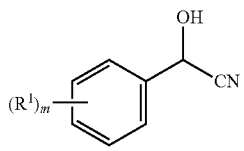
(1)

wherein $R^1$ independently represents an optionally-substituted alkyl group, an optionally-substituted alkenyl group, an optionally-substituted alkynyl group, an optionally-substituted alkoxy group, an optionally-substituted phenyl group, an optionally-substituted phenoxy group, an optionally-substituted amino group, a hydroxy group, a nitro group or a halogen atom, and m represents an integer of 0 to 5; and Step II of mixing a compound obtained in Step I, represented by Formula (3):

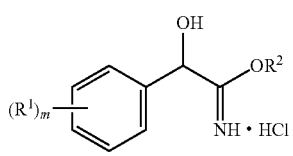
(3)

wherein $R^1$, $R^2$ and m each represent the same meanings as defined above with water.

[2] The method according to [1], wherein m is 1 in Formula (1).

[3] The method according to [1] or [2], wherein $R^1$ is represented by Formula (5) as follows:

$-CH_2OR^3$ (5)

wherein $R^3$ represents an optionally-substituted phenyl group, in Formula (1).

[4] The method according to any one of [1] to [3], wherein the compound represented by Formula (1) is 2-(2,5-dimethylphenoxymethyl)mandelonitrile.

[5] The method according to any one of [1] to [4], wherein the content of the hydrogen chloride is from 20 to 60 parts by weight relative to 100 parts by weight of the solution.

[6] The method according to any one of [1] to [5], wherein the organic solvent is an aromatic hydrocarbon.

[7] A method for producing a compound represented by Formula (3):

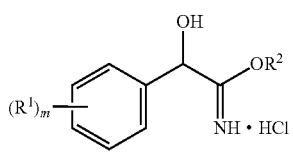
(3)

wherein $R^1$, $R^2$ and m each represent the same meanings as defined below, which comprises a step of adding a solution in which hydrogen chloride is dissolved in an alcohol represented by Formula (2) as follows:

$R^2OH$ (2)

wherein $R^2$ represents an alkyl group having 1 to 4 carbon atoms, to a mixture containing an organic solvent and a compound represented by Formula (1) as follows:

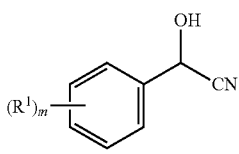
(1)

wherein $R^1$ independently represents an optionally-substituted alkyl group, an optionally-substituted alkenyl group, an optionally-substituted alkynyl group, an optionally-substituted alkoxy group, an optionally-substituted phenyl group, an optionally-substituted phenoxy group, an optionally-substituted amino group, a hydroxy group, a nitro group or a halogen atom, and m represents an integer of 0 to 5.

[8] An intermediate which is represented by Formula (3):

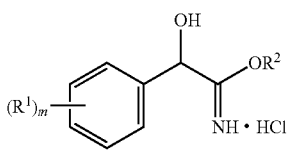
(3)

wherein $R^1$ independently represents an optionally-substituted alkyl group, an optionally-substituted alkenyl group, an optionally-substituted alkynyl group, an optionally-substituted alkoxy group, an optionally-substituted phenyl group, an optionally-substituted phenoxy group, an optionally-substituted amino group, a hydroxy group, a nitro group or a halogen atom, m represents an integer of 0 to 5, and $R^2$ represents an alkyl group having 1 to 4 carbon atoms
for the production of a compound represented by Formula (4):

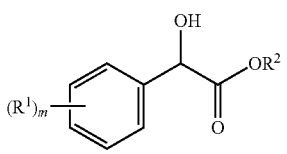
(4)

wherein $R^1$, $R^2$ and m each represent the same meanings as defined above.

[9] Use of a compound which is represented by Formula (3):

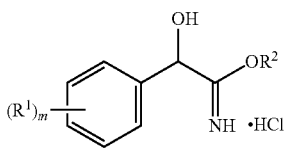
(3)

wherein $R^1$, $R^2$ and m each represent the same meanings as defined below, in the production of a compound represented by Formula (4):

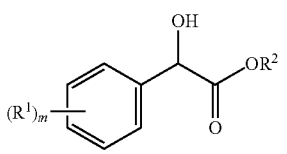
(4)

wherein $R^1$ independently represents an optionally-substituted alkyl group, an optionally-substituted alkenyl group, an optionally-substituted alkynyl group, an optionally-substituted alkoxy group, an optionally-substituted phenyl group, an optionally-substituted phenoxy group, an optionally-substituted amino group, an hydroxy group, an nitro group or a halogen atom, m represents an integer of 0 to 5, and $R^2$ represents an alkyl group having 1 to 4 carbon atoms.

[10] A compound represented by Formula (3-1):

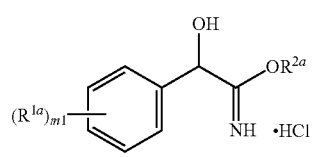
(3-1)

wherein $R^{1a}$ independently represents —$CH_2$—$R^{3a}$, $R^{3a}$ represents an optionally-substituted alkoxy group or an optionally-substituted phenoxy group, m1 represents an integer of 0 to 5, and $R^{2a}$ represents an alkyl group having 1 to 4 carbon atoms.

EFFECTS OF THE INVENTION

According to the present invention, an α-hydroxyester compound can be produced in a satisfactory yield.

MODE FOR CARRYING OUT THE INVENTION

The present invention will be described in detail below.

In the present invention, the number of carbon atoms of the optionally-substituted alkyl group is usually from about 1 to 12. The alkyl group may be a non-substituted alkyl group, or may be an alkyl group substituted with a halogen atom, a hydroxy group, a nitro group, an amino group, an alkoxy group, a phenoxy group or the like. Examples of the non-substituted alkyl group include a methyl group, an ethyl group, an n-propyl group, an isopropyl group, an n-butyl group, an isobutyl group, an s-butyl group, a t-butyl group, an n-pentyl group, an n-hexyl group, an n-octyl group and an n-decyl group. Examples of the substituted alkyl group include a haloalkyl group such as a monofluoromethyl group, a difluoromethyl group or a trifluoromethyl group, a hydroxymethyl group, a nitromethyl group and an aminomethyl group.

Examples of the alkyl group substituted with an alkoxy group include alkyl groups having an alkoxy group having 1 to 4 carbon atoms as a substituent, such as a methoxymethyl group, an ethoxymethyl group, an n-propoxymethyl group, an isopropoxymethyl group, an n-butoxymethyl group, an isobutoxymethyl group, an s-butoxymethyl group and a t-butoxymethyl group. Examples of the alkyl group substituted with a phenoxy group include groups represented by Formula (5) as follows:

—$CH_2OR^3$ (5)

wherein $R^3$ represents an optionally-substituted phenyl group. Examples of $R^3$ include a non-substituted phenyl group, and a phenyl group having one or more substituents such as an alkyl group, a halogen atom, a hydroxy group, a nitro group and an alkoxy group. In the present description, the substituted phenyl group may have 1 to 5 substituents, preferably 1 to 3 substituents, and more preferably 1 to 2 substituents. Examples of the above phenyl group having a substituent include phenyl groups substituted with an alkyl group having 1 to 4 carbon atoms, such as a 2-methylphenyl group, a 3-methylphenyl group, a 4-methylphenyl group, a 2,3-dimethylphenyl group, a 2,4-dimethylphenyl group, a 2,5-dimethylphenyl group and a 2,6-dimethylphenyl group; halogen-substituted phenyl groups such as a 2-chlorophenyl group, a 3-chlorophenyl group and a 4-chlorophenyl group; hydroxy-substituted phenyl groups such as a 2-hydroxyphenyl group, a 3-hydroxyphenyl group and a 4-hydroxyphenyl group; nitro group-substituted phenyl groups such as a 2-nitrophenyl group, a 3-nitrophenyl group and a 4-nitrophenyl group; and phenyl groups substituted with an alkoxy group having 1 to 4 carbon atoms, such as a 2-methoxyphenyl group, a 3-methoxyphenyl group and a 4-methoxyphenyl group.

In the present invention, the number of carbon atoms of the optionally-substituted alkenyl group is usually from about 2 to 12. The alkenyl group may be a non-substituted alkenyl group, or may be an alkenyl group substituted with a halogen atom, a hydroxy group, a nitro group, an amino group, an alkoxy group or the like. Examples of the non-substituted alkenyl group include a vinyl group, an allyl group, a 1-butenyl group, a 1-pentenyl group, a 1-hexenyl group and a 1-octenyl group. Examples of the substituted alkenyl group include a 3-hydroxy-1-propenyl group, a 3-nitro-1-propenyl group, a 3-amino-1-propenyl group and a 3-methoxy-1-propenyl group.

In the present invention, the number of carbon atoms of the alkynyl group is usually from about 2 to 12. The alkynyl group may be a non-substituted alkynyl group, or may be an alkynyl group substituted with a halogen atom, a hydroxy group, a nitro group, an amino group, an alkoxy group or the like. Examples of the non-substituted alkynyl group include a 1-ethynyl group, a propargyl group, a 1-butynyl group, a 1-pentynyl group, a 1-hexynyl group and a 1-octynyl group. Examples of the substituted alkynyl group include a 3-hydroxy-1-propynyl group, a 3-nitro-1-propynyl group, a 3-amino-1-propynyl group and a 3-methoxy-1-propynyl group.

In the present invention, the number of carbon atoms of the optionally-substituted alkoxy group is usually from about 1 to 12. The alkoxy group may be a non-substituted alkoxy group, or may be an alkoxy group substituted with a halogen atom, a hydroxy group, a nitro group, an amino group, an alkoxy group or the like. Examples of the non-substituted alkoxy group include a methoxy group, an ethoxy group, an n-propoxy group, an isopropoxy group, an n-butoxy group, an isobutoxy group, an s-butoxy group, a t-butoxy group, a 1-hexyloxy group and a 1-octyloxy group. Examples of the substituted alkoxy group include a trifluoromethyloxy group, a hydroxymethyloxy group, a nitromethyloxy group, an aminomethyloxy group and a methoxymethyloxy group.

In the present invention, examples of the optionally-substituted phenyl group can include the same substituents as those for $R^3$ described above.

In the present invention, the number of carbon atoms of the optionally-substituted phenoxy group is usually from about 1 to 12. The phenoxy group may be a non-substituted phenoxy group, or may be a phenoxy group substituted with an alkyl group, a halogen atom, a hydroxy group, a nitro group, an alkoxy group or the like. In the present description, the phenoxy group having a substituent may have 1 to 5 substituents, preferably 1 to 3 substituents, and more preferably 1 to 2 substituents. Examples of the substituted phenoxy group include phenyl groups substituted with an alkyl group having 1 to 4 carbon atoms, such as a 2-methylphenoxy group, a 3-methylphenoxy group, a 4-methylphenoxy group, a 2,3-dimethylphenoxy group, a 2,4-dimethylphenoxy group, a 2,5-dimethylphenoxy group and a 2,6-dimethylphenoxy group; halogen-substituted phenyl groups such as a 2-chlorophenoxy group, a 3-chlorophenoxy group and a 4-chlorophenoxy group; hydroxy-substituted phenyl group such as a 2-hydroxyphenoxy group, a 3-hydroxyphenoxy group and a 4-hydroxyphenoxy group; nitro group-substituted phenyl groups such as a 2-nitrophenoxy group, a 3-nitrophenoxy group and a 4-nitrophenoxy group; and phenyl groups substituted with an alkoxy group having 1 to 4 carbon atoms, such as a 2-methoxyphenoxy group, a 3-methoxyphenoxy group and a 4-methoxyphenoxy group.

In the present invention, examples of the optionally-substituted amino group include non-substituted amino groups; and amino groups substituted with an alkyl having 1 to 4 carbon atoms, such as a methylamino group and a dimethylamino group.

In the present invention, examples of the halogen atom include a fluorine atom, a chlorine atom, a bromine atom and an iodine atom.

In the present invention, a mandelonitrile compound (1) is preferably a compound in which m=1 in Formula (1). The above $R^1$ is preferably located at the 2-position of an aromatic ring.

The mandelonitrile compound (1) is preferably a compound in which $R^1$ is a group represented by Formula (5):

—CH$_2$OR$^3$ (5)

($R^3$ represents an optionally-substituted phenyl group), an alkoxy group having 1 to 4 carbon atoms or a phenyl group, and more preferably a compound in which $R^1$ is a group represented by the above formula (5).

The mandelonitrile compound (1) is more preferably 2-(5-methylphenoxymethyl)mandelonitrile, 2-(2-methylphenoxymethyl)mandelonitrile, 2-(2,5-dimethylphenoxymethyl)mandelonitrile, 2-(phenoxymethyl)mandelonitrile, 2-methoxymandelonitrile, 2-ethoxymandelonitrile, 2-propoxymandelonitrile, 2-butoxymandelonitrile or 2-phenylmandelonitrile.

The above mandelonitrile compound (1) is particularly preferably 2-(2,5-dimethylphenoxymethyl)mandelonitrile [a compound in which m=1, and $R^1$ is substituted at the 2-position of an aromatic ring and is also a 2,5-dimethylphenoxymethyl group in Formula (1)].

Examples of the organic solvent used in the present invention include aromatic hydrocarbon such as benzene, toluene, xylene and chlorobenzene; aliphatic hydrocarbons such as n-hexane and n-heptane; alicyclic hydrocarbons such as cyclopentane and cyclohexane; ketones such as methylethylketone and methylisobutylketone; and ethers such as diethylether, dibutylether, tetrahydrofuran and tetrahydropyran. If necessary, two or more kinds of the organic solvents can be used. Among these organic solvents, aromatic hydrocarbons are preferred and aromatic hydrocarbons substituted with an alkyl group having 1 to 3 carbon atoms are more preferred. The use amount of the organic solvent is usually 0.5 part by weight or more, and preferably 1 part by weight or more, relative to 1 part by weight of the mandelonitrile compound (1), and the upper limit of the use amount is usually 10 parts by weight, preferably 5 parts by weight, and more preferably 3 parts by weight.

The production method of the present invention includes Step I of adding a solution in which hydrogen chloride is dissolved in an alcohol (2) (hereinafter, this solution is referred to as "solution of alcohol (2)") to a mixture containing an organic solvent and a mandelonitrile compound (1).

By adding the solution of alcohol (2) to the mixture containing an organic solvent and a mandelonitrile compound (1), efficiency of a reaction of converting the mandelonitrile compound (1), hydrogen chloride and the alcohol (2) into an imino ester (3) becomes satisfactory. Therefore, the imino ester (3) can be obtained by Step I at high conversion ratio and selectivity.

The alcohol (2) is represented by Formula (2):

$$R^2OH \quad (2)$$

wherein $R^2$ represents an alkyl group having 1 to 4 carbon atoms.

In the present invention, examples of $R^2$ include a methyl group, an ethyl group, an n-propyl group, an isopropyl group, an n-butyl group, an isobutyl group, an s-butyl group and a t-butyl group.

Specific examples of the alcohol (2) include methanol, ethanol, 1-propanol, 2-propanol, 1-butanol and 2-butanol. The alcohol (2) is preferably methanol.

The content of hydrogen chloride in the solution of alcohol (2) is usually 20 parts by weight or more, and preferably 40 parts by weight or more, relative to 100 parts by weight of the solution and the upper limit of the content is usually 60 parts by weight, and preferably 55 parts by weight, relative to 100, parts by weight of the solution.

The use amount of hydrogen chloride is usually 1 mol or more, and preferably 1.2 mol or more, per mol of the mandelonitrile compound (1) and the upper limit of the use amount is usually 5 mol, preferably 3 mol, and more preferably 2.5 mol, per mol of the mandelonitrile compound (1).

Examples of the method of adding the solution of alcohol (2) to a mixture containing an organic solvent and the mandelonitrile compound (1) include a method of adding the solution to the mixture at a time, and a method of adding dropwise the solution to the mixture little by little. Among these methods, the method of adding dropwise the solution to the mixture little by little is preferred, and the drop time is usually from 0.5 to 20 hours, and preferably from 1 to 10 hours. After the addition of the above solution to the above mixture, the mandelonitrile compound (1) can be sufficiently converted by continuously stirring while keeping warm. The warm time is usually from 0.5 to 20 hours, and preferably from 1 to 10 hours.

The temperature in Step I is usually −20° C. or higher, and preferably 0° C. or higher, and the upper limit of the temperature is usually 50° C., and preferably 30° C.

An imino ester (3) can be obtained by Step I. The imino ester (3) will be described hereinafter.

The production method of the present invention further includes Step II of mixing the above imino ester (3) with water. In Step II, an α-hydroxyester (4) can be obtained by reacting the imino ester (3) with water.

In Step II, since the imino ester (3) is mixed with water, the conversion ratio and selectivity of the α-hydroxyester (4) is very satisfactory. Namely, since the present production method include Steps I and II, the α-hydroxyester (4) can be produced from the mandelonitrile compound (1) with high yield and selectivity.

The use amount of water in Step II is usually 0.1 part by weight or more, preferably 0.5 part by weight or more, and more preferably 1 part by weight or more, relative to 1 part by weight of the solution of alcohol (2) used in Step I, and the upper limit of the use amount is usually 10 parts by weight, preferably 5 parts by weight, and more preferably 3 parts by weight, relative to 1 part by weight of the solution of alcohol (2).

Mixing of the above imino ester (3) and water may be performed by adding water to the isolated imino ester (3), or may be performed by adding water to the reaction mixture obtained from the reaction of Step I. Examples of the method of mixing the imino ester (3) and water include a method of adding water to the imino ester (3) or the reaction mixture at a time, and a mixture of adding dropwise water to the imino ester (3) or the reaction mixture little by little. In the case where water is added dropwise to the imino ester (3) or the reaction mixture little by little, the drop time of water is usually from 0.5 to 20 hours, and preferably from 1 to 10 hours. After mixing, the imino ester (3) can be sufficiently converted by continuously stirring while keeping warm. The warm time is usually from 0.5 to 20 hours, and preferably from 1 to 10 hours.

The temperature in Step II is usually 0° C. or higher, and preferably 5° C. or higher, and the upper limit of the temperature is usually 70° C., and preferably 60° C.

In Step II, the α-hydroxyester (4) can be isolated from the reaction mixture obtained by mixing the above imino ester (3) and water using a known method. Examples of the above isolation method include distillation and crystallization.

If necessary, the α-hydroxyester (4) obtained in Step II can be purified by conventionally known means. Examples of the purification method include oil-water separation Examples of preferred α-hydroxyester (4) include 1-[2-(2,5-dimethylphenoxymethyl)phenyl]-2-hydroxyacetic acid ester, 1-[2-(5-methylphenoxymethyl)phenyl]-2-hydroxyacetic acid ester, 1-[2-(2-methylphenoxymethyl)phenyl]-2-hydroxyacetic acid ester, 1-[2-(phenoxymethyl)phenyl]-2-hydroxyacetic acid ester, 1-(2-methoxyphenyl)-2-hydroxyacetic acid ester, 1-(2-ethoxyphenyl)-2-hydroxyacetic acid ester, 1-(2-propoxyphenyl)-2-hydroxyacetic acid ester, 1-(2-butoxyphenyl)-2-hydroxyacetic acid ester and 1-(2-biphenyl)-2-hydroxyacetic acid ester.

The above imino ester (3) is represented by Formula (3):

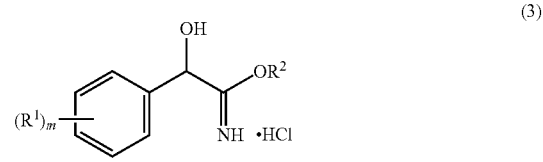

wherein $R^1$, $R^2$ and m each represent the same meanings as defined above.

The imino ester (3) is useful as an intermediate with satisfactory selectivity and yield in the production of the α-hydroxyester (4), particularly the production method of the present invention. Each of an intermediate, which is represented by Formula (3), for the production of an α-hydroxyester (4), and use of the compound represented by Formula (3) in the production of the α-hydroxyester (4) is one of the present invention.

In Formula (3), $R^1$, $R^2$ and m are preferably the same groups as in the respective substituents in the mandelonitrile compound (1) since the α-hydroxyester (4) is obtained in a high yield.

Examples of preferred imino ester (3) include 1-[2-(2,5-dimethylphenoxymethyl)phenyl]-1-hydroxy-2-methoxyethane iminium chloride, 1-[2-(5-methylphenoxymethyl)phenyl]-1-hydroxy-2-methoxyethane iminium chloride, 1-[2-(2-methylphenoxymethyl)phenyl]-1-hydroxy-2-methoxyethane iminium chloride, 1-[2-(phenoxymethyl)phenyl]-1-hydroxy-2-methoxyethane iminium chloride, 1-(2-methoxyphenyl)-1-hydroxy-2-methoxyethane iminium chloride, 1-(2-ethoxyphenyl)-1-hydroxy-2-methoxyethane iminium chloride, 1-(2-propoxyphenyl)-1-hydroxy-2-methoxyethane iminium chloride, 1-(2-butoxyphenyl)-1-hydroxy-2-methoxyethane iminium chloride and 1-(2-biphenyl)-1-hydroxy-2-methoxyethane iminium chloride.

The imino ester (3) can be obtained, for example, by Step I, as described above. A method for producing the imino ester (3), including Step I is also one of the present invention. The above imino ester (3) can be isolated from the reaction mixture obtained by a reaction in Step I using a conventionally known isolation method. Examples of the isolation method include distillation and crystallization. The obtained imino ester (3) can be analyzed, for example, by IR and NMR.

Among the above imino ester (3), a compound represented by Formula (3-1):

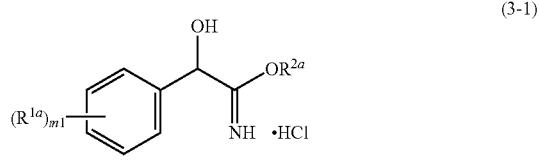

(3-1)

wherein $R^{1a}$ independently represents —$CH_2$—$R^{3a}$, $R^{3a}$ represents an optionally-substituted alkoxy group or an optionally-substituted phenoxy group, m1 represents an integer of 0 to 5, and $R^{2a}$ represents an alkyl group having 1 to 4 carbon atoms, is also one of the present invention.

The compound represented by Formula (3-1) is useful as an intermediate capable of producing an α-hydroxyester (4) with excellent selectivity.

In Formula (3-1), examples of the optionally-substituted alkoxy group and optionally-substituted phenoxy group each include groups mentioned as the above $R^1$.

In Formula (3-1), $R^{1a}$ is preferably —$CH_2$—$R^{3a}$ ($R^{3a}$=an optionally-substituted phenoxy group), and more preferably —$CH_2$—$R^{3a}$ ($R^{3a}$=a phenoxy group substituted with an alkyl group having 1 to 3 carbon atoms).

$R^{2a}$ preferably an alkyl group having 1 to 3 carbon atoms, and more preferably an alkyl group having 1 to 2 carbon atoms. m1 is preferably from 1 to 2, and more preferably 1. $R^{1a}$ is preferably located at the ortho-position to a substituent having an imino ester.

Examples of the compound represented by Formula (3-1) include 1-{2-[(di-C1-C4 alkyl)phenoxymethyl] phenyl}-1-hydroxy-2-methoxyethane iminium chloride, 1-{2-[(C1-C4 alkyl)phenoxymethyl] phenyl}-1-hydroxy-2-methoxyethane iminium chloride and 1-(phenoxymethyl)-1-hydroxy-2-methoxyethane iminium chloride, and preferably include 1-[2-(2,5-dimethylphenoxymethyl)phenyl]-1-hydroxy-2-methoxyethane iminium chloride and 1-(2-phenoxymethyl)-1-hydroxy-2-methoxyethane iminium chloride.

The compound represented by Formula (3-1) can be prepared in the same manner as in the case of the compound represented by Formula (3), and can be obtained with particularly high selectivity in the method of Step I.

EXAMPLES

Examples of the present invention will be described below. A conversion ratio of the mandelonitrile compound (1) and a yield of the α-hydroxyester (4) were determined by analyzing the composition of each reaction mixture through high performance liquid chromatography (apparatus used: Shimadzu LC-10A, manufactured by Shimadzu Corporation).

Example 1

In a 3-L flask, 255.9 g (0.91 mol) of 2-(2,5-dimethylphenoxymethyl)mandelonitrile and 469.0 g of xylene were charged and, after mixing, the obtained mixture i was cooled to 7° C. while stirring. Next, to the mixture, 160.1 g (mol number of hydrogen chloride: 2.06 mol) of a methanol solution containing 47% by weight hydrogen chloride was added dropwise over 2 hours and then the obtained mixture ii was stirred while keeping warm at 7° C. for 2 hours to obtain the reaction mixture containing 1-[2-(2,5-dimethylphenoxymethyl)phenyl]-1-hydroxy-2-methoxyethane iminium chloride. A conversion ratio of 2-(2,5-dimethylphenoxymethyl) mandelonitrile was 99.2%.

After adding dropwise 320.1 g of water to the above reaction mixture over 1 hour, the obtained mixture iii was heated to 50° C. and then stirred while keeping warm for 1 hour to obtain a two-layered (oil-water) mixed solution. A conversion ratio of 2-(2,5-dimethylphenoxymethyl)mandelonitrile was 99.5% and a yield of methyl 2-[2-(2,5-dimethylphenoxymethyl)]-2-hydroxyacetate was 96.2% .

Example 2

The same operation as in Example 1 was performed to obtain the reaction mixture containing 1-[2-(2,5-dimethylphenoxymethyl)phenyl]-1-hydroxy-2-methoxyethane iminium chloride. Next, the reaction mixture was filtered and the obtained solid was dried to obtain a white powdered 1-[2-(2,5-dimethylphenoxymethyl)phenyl]-1-hydroxy-2-methoxyethane iminium chloride.

Data of mass spectrum (MS), NMR spectrum, infrared spectroscopy spectrum (IR) of the compound were as follows. MS: ESI(+) 300.4(M+H$^+$)

$^1$H-NMR (ppm, d-MeOH): 2.16(s,3H), 2.30(s,3H), 4.07(s, 3H), 5.11(d,1H), 5.31(d,1H), 5.89(s,1H), 6.5-8.0(m,7H) $^{13}$C-NMR (ppm, d-MeOH): 16.06, 21.44, 68.79, 70.42, 113.71, 122.61, 124.59, 128.77, 129.30, 130.00, 130.72, 131.25, 131.55, 136.88, 137.26, 137.90, 157.88, 183.91

IR (cm$^{-1}$): 3188, 2833, 1651, 1613, 1585, 1511, 1444, 1407, 1269, 1256, 1159, 1134, 1088, 1060, 994, 936, 876, 851, 806, 747

Each measurement was performed under the following conditions.

Mass spectrum (MS): 1 µg of a sample was analyzed by ESI+ using Q-T of micro (manufactured by Waters Corporation).
NMR spectrum: 10 mg of a sample was dissolved in 600 mg of d-MeOH and then the measurement was performed by NMR PS400WB (manufactured by Varian, 400 MHz).
Infrared spectroscopy spectrum (IR): The measurement was performed by Magna760 (manufactured by Nicolet Inc., ATR).

Example 3

In a 100-mL flask, 9 g (0.051 mol) of 2-ethoxymandelonitrile and 13.5 g of xylene were charged and, after mixing, the obtained mixture i-a was cooled. to 7° C. while stirring. Next, to the mixture, 7.89 g (mol number of hydrogen chloride: 0.1 mol) of a methanol solution containing 47% by weight hydrogen chloride was added dropwise over 2 hours and then the obtained mixture ii-a was stirred while keeping warm at 7° C. for 2 hours to obtain the reaction mixture containing 1-(2-ethoxyphenyl)-1-hydroxy-2-methoxyethane iminium chloride. A conversion ratio of 2-ethoxymandelonitrile was 88.6%

After adding dropwise 15.78 g of water to the above reaction mixture over 1 hour, the obtained mixture iii-a was heated to 50° C. and then stirred while keeping warm for 1 hour to obtain a two-layered oil-water mixed solution. The aqueous layer was separated and 15.78 g of 1% sulfuric acid was added to the oil layer and they were mixed, followed by liquid separation. To the obtained oil layer, 15.78 g of water was added and mixed with it, followed by liquid separation to obtain the oil layer. The oil layer was concentrated under reduced pressure at 70° C. to obtain 9.3 g of methyl 2-(2-ethoxyphenyl)-2-hydroxyacetate. A yield was 87.1%.

Example 4

In a 100-mL flask, 3 g (0.014 mol) of 2-phenylmandelonitrile and 4.5 g of xylene were charged and, after mixing, the obtained mixture i-b was cooled to 7° C. while stirring. Next, to the mixture, 2.23 g (mole number of hydrogen chloride: 0.028 mol) of a methanol solution containing 47% by weight hydrogen chloride was added dropwise over 2 hours and then the obtained mixture ii-b was stirred while keeping warm at 7° C. for 1 hour to obtain the reaction mixture containing 1-(2-biphenyl)-1-hydroxy-2-methoxyethane iminium chloride. A conversion ratio of 2-phenylmandelonitrile was 100%.

After adding dropwise 4.45 g of water to the above reaction mixture over 1 hour, the obtained solution was heated to 50° C. and then stirred while keeping warm for 1 hour to obtain a two-layered oil-water mixed solution. The aqueous layer was separated and 4.45 g of 1% sulfuric acid was added to the oil layer, followed by mixing and then separation it to obtain an oil layer. To the obtained oil layer, 4.45 g of water was added, followed by mixing and further liquid separation to obtain the oil layer. The oil layer was concentrated under reduced pressure at 70° C. to obtain 2.87 g of methyl 2-(2-biphenyl)-2-hydroxyacetate. A yield was 82.6%.

Comparative Example 1

In a 3-L flask, 55.62 g (0.2 mol) of 2-(2,5-dimethylphenoxymethyl)mandelonitrile and 83.43 g of methanol were charged and, after mixing, the obtained mixture i-c was cooled to 7° C. while stirring. Next, to the mixture, 16.38 g (0.45 mol) of hydrogen chloride gas was fed over 2 hours to obtain the reaction mixture containing 1-[2-(2,5-dimethylphenoxymethyl)phenyl]-1-hydroxy-2 -methoxyethane iminium chloride. A conversion ratio of 2-(2,5-dimethylphenoxymethyl)mandelonitrile was 100%. However, by-products other than the above iminium salt were observed in a considerable number.

After adding dropwise 32.75 g of water to the above reaction mixture over 1 hour, the obtained mixture ii-c was heated to 50° C. and then stirred while keeping warm for 1 hour to obtain a two-layered oil-water mixed solution. A conversion ratio of 2-(2,5-dimethylphenoxymethyl)mandelonitrile was 100% and a yield of methyl 2-[2-(2,5-dimethylphenoxymethyl)]-2-hydroxyacetate was 57.1%.

Comparative Example 2

In a 500-ml flask, 55.62 g (0.2 mol) of 2-(2,5-dimethylphenoxymethyl)mandelonitrile, 71 g of xylene, 19 g of methanol and 39.14 g of water were charged and, after mixing, the obtained mixture i-d was heated to 40° C. while stirring. Next, to the mixture, 7.94 g (0.22 mol) of a hydrogen chloride gas was fed over 1 hour. Next, the obtained mixture ii-d was heated at 89° C. for 4 hours and then cooled to room temperature to obtain a two-layered (oil-water) mixed solution. A conversion ratio of 2-(2,5-dimethylphenoxymethyl)mandelonitrile was 4.4% and a yield of methyl 2-[2-(2,5-dimethylphenoxymethyl)]-2-hydroxyacetate was 3.1%.

INDUSTRIAL APPLICABILITY

According to the production method of the present invention, an α-hydroxyester compound can be produced in a satisfactory yield.

The invention claimed is:

1. A method for producing a compound represented by Formula (4):

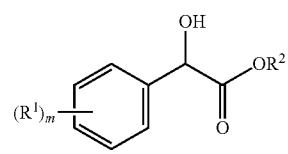

wherein $R^1$, $R^2$ and m each represent the same meanings as defined below, which comprises Step I of adding a solution in which hydrogen chloride is dissolved in an alcohol represented by Formula (2):

wherein $R^2$ represents an alkyl group having 1 to 4 carbon atoms, to a mixture containing an organic solvent and a compound represented by Formula (1):

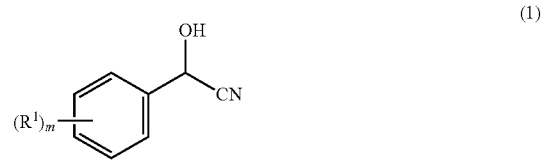

wherein $R^1$ is represented by Formula (5) as follows:

wherein $R^3$ represents an optionally-substituted phenyl group, and m represents an integer of 0 to 5; and Step II of mixing a compound obtained in Step I, represented by Formula (3):

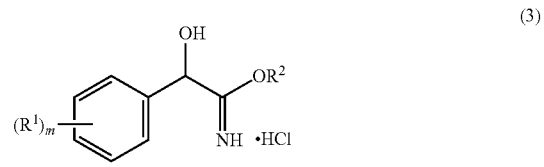

wherein $R^1$, $R^2$ and m each represent the same meanings as defined above, with water.

2. The method according to claim 1, wherein m is 1 in Formula (1).

3. The method according to claim 1, wherein the compound represented by Formula (1) is 2-(2,5-dimethylphenoxymethyl)mandelonitrile.

4. The method according to claim 1, wherein the content of the hydrogen chloride is from 20 to 60 parts by weight relative to 100 parts by weight of the solution.

5. The method according to claim 1, wherein the organic solvent is an aromatic hydrocarbon.

6. A method for producing a compound represented by Formula (3):

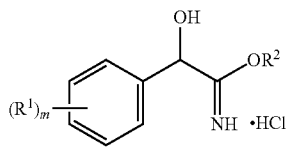

(3)

wherein $R^1$, $R^2$ and m each represent the same meanings as defined below, which comprises a step of adding a solution in which hydrogen chloride is dissolved in an alcohol represented by Formula (2) as follows:

$$R^2OH \quad (2)$$

wherein $R^2$ represents an alkyl group having 1 to 4 carbon atoms, to a mixture containing an organic solvent and a compound represented by Formula (1) as follows:

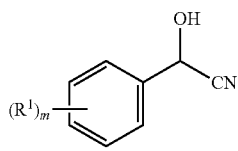

(1)

wherein $R^1$ is represented by Formula (5) as follows:

$$-CH_2OR^3 \quad (5)$$

wherein $R^3$ represents an optionally-substituted phenyl group, and m represents an integer of 1 to 5.

7. An intermediate which is represented by Formula (3):

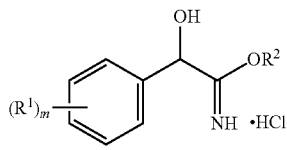

(3)

wherein $R^1$ is represented by Formula (5) as follows:

$$-CH_2OR^3 \quad (5)$$

wherein $R^3$ represents an optionally-substituted phenyl group, m represents an integer of 1 to 5, and $R^2$ represents an alkyl group having 1 to 4 carbon atoms for the production of a compound represented by Formula (4):

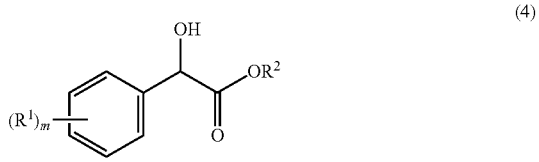

(4)

wherein $R^1$, $R^2$ and m each represent the same meanings as defined above.

8. A compound represented by Formula (3-1):

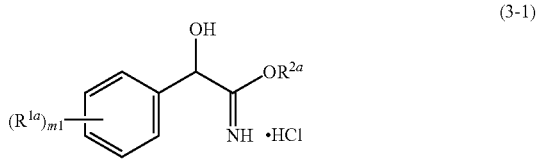

(3-1)

wherein $R^{1a}$ independently represents $-CH_2-R^{3a}$, $R^{3a}$ represents an optionally-substituted alkoxy group or an optionally-substituted phenoxy group, m1 represents an integer of 1 to 5, and $R^{2a}$ represents an alkyl group having 1 to 4 carbon atoms.

\* \* \* \* \*